(12) United States Patent
Knisley

(10) Patent No.: US 6,936,068 B1
(45) Date of Patent: Aug. 30, 2005

(54) INFLATABLE PROSTHETIC DEVICE

(76) Inventor: Melvin E. Knisley, 714 S. Shannon St., Santa Ana, CA (US) 92704

( * ) Notice: Subject to any disclaimer, the term of this patent is extended or adjusted under 35 U.S.C. 154(b) by 56 days.

(21) Appl. No.: 10/633,443

(22) Filed: Aug. 4, 2003

(51) Int. Cl.$^7$ ................................. A61F 2/52
(52) U.S. Cl. ....................................... 623/7
(58) Field of Search ................... 623/11.1, 7, 8, 623/11.11, 23.64–23.68

(56) References Cited

U.S. PATENT DOCUMENTS

| | | | |
|---|---|---|---|
| 2,698,436 A | * 1/1955 | Bernhardt | ................ 623/7 |
| 3,600,718 A | 8/1971 | Boone | |
| 3,811,133 A | 5/1974 | Harris | |
| 3,896,506 A | 7/1975 | Hankin et al. | |
| 4,143,428 A | * 3/1979 | Cohen | ................ 623/8 |
| 4,157,085 A | * 6/1979 | Austad | ............... 128/898 |
| 4,205,401 A | * 6/1980 | Frisch | ................ 623/8 |
| 4,428,364 A | * 1/1984 | Bartolo | ............... 128/897 |
| 4,429,068 A | * 1/1984 | Nakahira | ............... 524/302 |
| 4,624,671 A | 11/1986 | Kress | |
| 4,643,733 A | * 2/1987 | Becker | ................ 623/8 |
| 4,671,255 A | * 6/1987 | Dubrul et al. | ........... 128/899 |
| 4,826,501 A | * 5/1989 | Grundei | ................ 623/8 |
| 5,066,302 A | 11/1991 | Rice | |
| 5,104,409 A | * 4/1992 | Baker | ................ 623/8 |
| 5,370,688 A | 12/1994 | Schulz et al. | |
| 5,496,370 A | * 3/1996 | Hamas | ............ 623/23.67 |
| 5,697,974 A | * 12/1997 | Wang | ................ 623/7 |
| 5,823,852 A | * 10/1998 | Chu | ................ 450/38 |
| 6,074,421 A | * 6/2000 | Murphy | ................ 623/8 |
| 6,099,566 A | * 8/2000 | Vonderharr et al. | ........ 623/8 |
| 6,162,251 A | * 12/2000 | Kredovski | ................ 623/8 |
| 6,520,989 B1 | * 2/2003 | Eaton | ................ 623/7 |

* cited by examiner

Primary Examiner—David J. Isabella

(57) ABSTRACT

An inflatable prosthetic breast for wearing against an outer surface of a chest includes a housing having a back wall having a peripheral edge. A front wall is attached to and extends along a length of the peripheral edge such that an inner space is defined between the front and back walls. The front wall has a convex shape such that the front wall extends outwardly away from the back wall. The housing has an opening therein. The back wall and the front wall comprise a latex material has a thickness generally between 0.08 mm and 2.0 mm. A plug is removably extendable into opening. A fluid may be selectively added into or removed from the housing until the housing has a desired size.

10 Claims, 2 Drawing Sheets

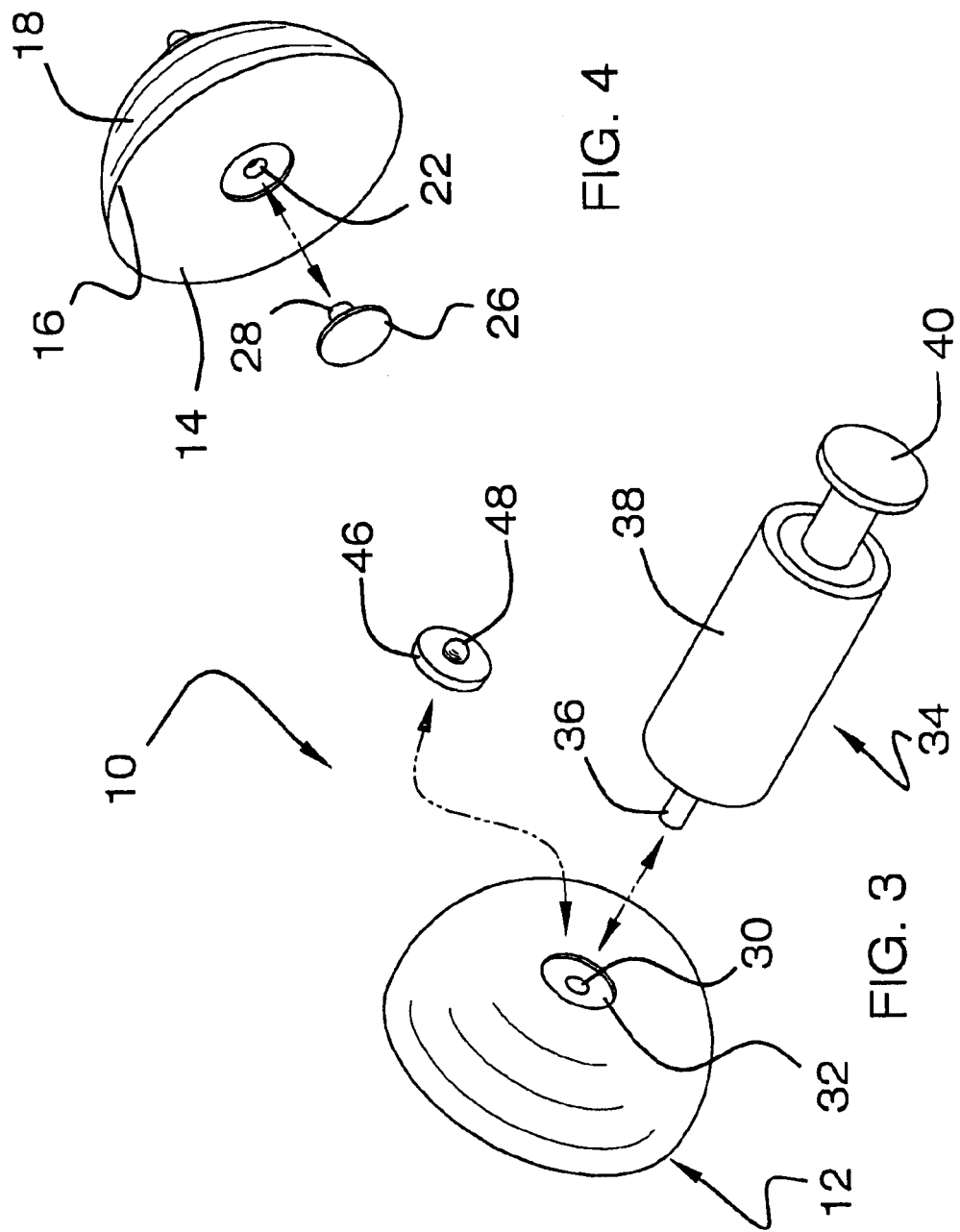

INFLATABLE PROSTHETIC DEVICE

BACKGROUND OF THE INVENTION

1. Field of the Invention

The present invention relates to prosthetic breasts and more particularly pertains to a new prosthetic breast that is positionable against the outer surface of a chest and has adjustable size allowances to provide the appearance of a natural breast.

2. Description of the Prior Art

The use of prosthetic breasts is known in the prior art. U.S. Pat. No. 4,624,671 describes a device that is surgically implanted and whose size may be altered. A general problem with these types of devices is that they require expensive and painful surgeries and these device may eventually fail and require additional surgeries. Another type of prosthetic breast is U.S. Pat. No. 3,811,133 having an outer shell which encases wadded fibers for giving weight and structure to the prosthetic device. These types of devices are generally alike in that, in order to attempt to replicate the feeling of a natural breast, they incorporate exotic materials that feel like skin and include expensive filling materials. Because of the materials used, these prosthetics generally cost several hundred dollars.

While these devices fulfill their respective, particular objectives and requirements, the need remains for a device that is not only more economical than the previous types of devices, but also allows the user of the device to selectively, in a safe and efficient manner, to alter the size of the device.

SUMMARY OF THE INVENTION

The present invention meets the needs presented above by incorporating a housing, or shell, having the shape of a breast, that is constructed of a latex material. The latex material may be filled with a liquid, preferably water, so that it may be selectively adjusted for size to ensure that it resembles a remaining breast. The use of latex keeps the cost of the device very low while allowing the appearance and general feel of the device to match that of a natural breast when the device is positioned within a brazier and covered by clothing.

Another object of the present invention is to provide a new prosthetic breast that includes an aperture in the front of the housing for easy adjustments of the size of the device while it is against the chest of the wearer of the device.

Still another object of the present invention is to provide a new prosthetic breast that includes a one-way valve positioned in the aperture to prevent leakages outwardly of the device.

Yet another object of the present invention is to provide a new prosthetic breast that includes a cloth encasement for positioning over the device to offer the wearer of the device some comfort from the latex and the temperature of the fluid positioned within the housing.

To this end, the present invention generally comprises a housing having a back wall having a peripheral edge. A front wall is attached to and extends along a length of the peripheral edge such that an inner space is defined between the front and back walls. The front wall has a convex shape such that the front wall extends outwardly away from the back wall. The housing has an opening therein. The back wall and the front wall comprise a latex material has a thickness generally between 0.08 mm and 2.0 mm. A plug is removably extendable into opening. A fluid may be selectively added into or removed from the housing until the housing has a desired size.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a schematic perspective view of the present invention.

FIG. 4 is a schematic rear perspective view of the present invention.

DESCRIPTION OF THE PREFERRED EMBODIMENT

Figure 1:
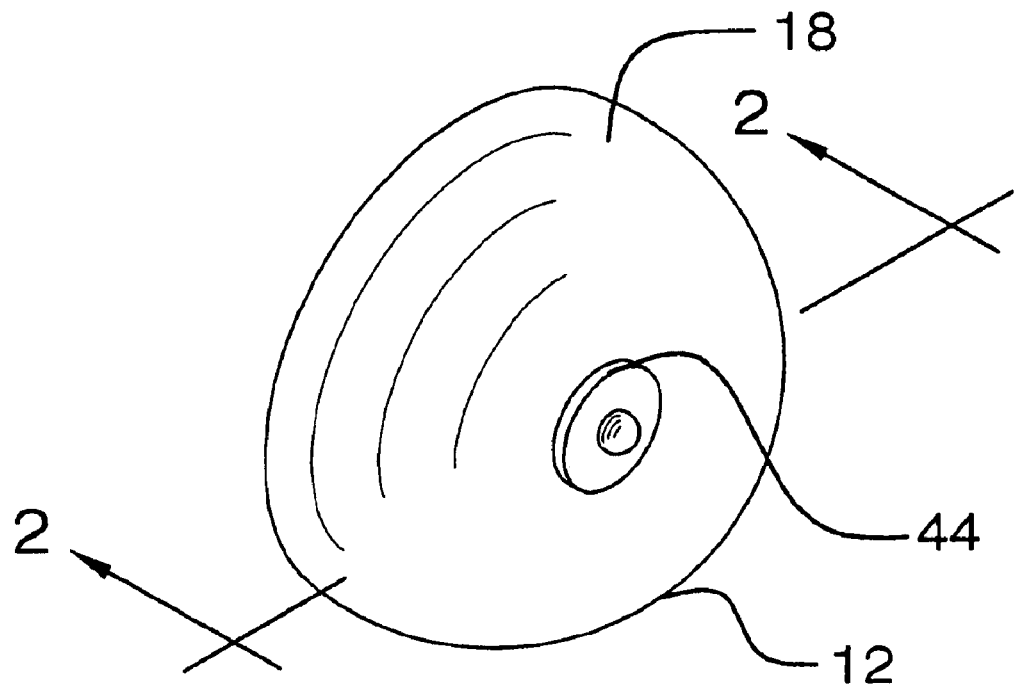
FIG. 1 is a schematic perspective view of a inflatable prosthetic device according to the present invention.

With reference now to the drawings, and in particular to FIGS. 1 through 4 thereof, a new prosthetic breast embodying the principles and concepts of the present invention and generally designated by the reference numeral 10 will be described.

As best illustrated in FIGS. 1 through 4, the inflatable prosthetic device 10 generally comprises a housing 12 having a back wall 14 having a peripheral edge 16. A front wall 18 is attached to and extends along a length of the peripheral edge 16 such that an inner space 20 is defined between the front 18 and back 14 walls. The front wall 18 has a convex shape such that the front wall 18 extends outwardly away from the back wall 14. The housing 12 has an opening 22 therein. A plug 24 is removably extendable into opening 22. The plug 24 is conventional however it is preferred that it includes a flap 26 with a bulbous portion 28 thereon wherein the bulbous portion 28 is extended into and sealed with the opening 22 while the flap 26 is generally flush with the back wall 14. The opening 22 is positioned in the back wall 14. The back wall 14 and the front wall 18 comprise a latex material having a thickness generally between 0.08 mm and 2.0 mm. The latex has an ultimate elongation capability greater than 400% and a tensile strength greater than 12 Mpa. Ideally, the latex comprises a nitrile polymer of the type used for nitrile examination gloves. Natural rubber latex may also be used, however it has been found that such material may cause allergic reactions and the wear properties of nitrile polymers is such that nitrile is preferred. The back wall 14 has perimeter length generally between 25 cm and 50 cm. A maximum distance between inner surfaces of the front 18 and back 14 walls is generally between 6 cm and 12 cm when the front 18 and back 14 walls are in a relaxed state, meaning that the latex is not being elongated in any direction.

The front wall 18 has an aperture 30 extending therein. The aperture 30 is generally centrally located in the front wall 18 and is preferably positioned within a generally circular depression 32 in an outer surface of the front wall 18. An injector 34 for selectively injecting fluid into the housing includes a nozzle 36 fluidly coupled to a container 38, or barrel. The nozzle 36 is removably extendable into the aperture 30 for delivering fluid from the container 38 into the housing 12. The fluid may be forced into the housing 12 using a syringe-type plunger 40 positioned opposite of the nozzle 36. Preferably, the nozzle 36 has the same size as the aperture 30 so that as it is inserted into the aperture 30, a seal forms around the nozzle 36 to prevent leakage around the nozzle 36. Ideally, a one way valve 42 is fluidly coupled to the aperture 30 and is positioned within the inner space 20 for preventing fluid within the housing 12 from exiting the housing 12 through the aperture 30.

A covering 44 is selectively positioned over the aperture 30 for closing it. The covering 44 includes a disc member 46 having a shape adapted for positioning within the depression 32, which is preferably circular. The disc member 46 has a greater thickness than a depth of the depression 32 such that the disc 46 extends above the outer surface of the 25 front wall 18 when the disc 46 is positioned within the depression 32. A nub 48 is attached to the disc 46 and is generally centered thereon such that the nub 48 extends away from the housing 12 when the disc 46 is positioned within the depression 32.

Figure 2:
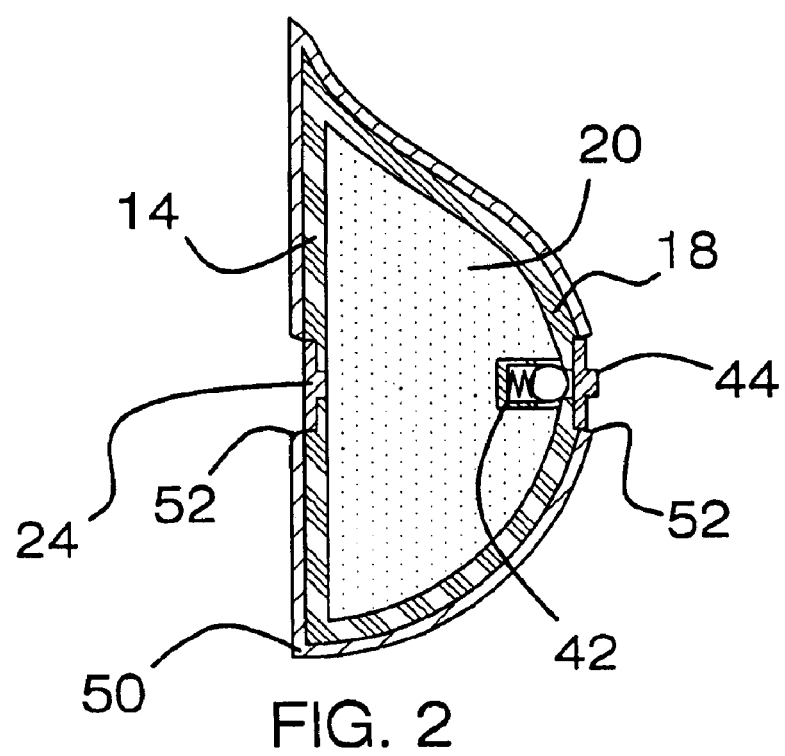
FIG. 2 is a schematic cross-sectional view of the present invention and including a covering of the present invention.

A encasement 50, only shown in FIG. 2 as a cross-section, is preferably positioned over the housing 12 to protect the wearer of the device from the latex and from the temperature of any fluid within the housing 12. The encasement 50 comprises an elastic cloth material, such as nylon. The encasement 50 has at least one opening 52, and preferably a pair of openings, therein. The opening 52 may be used for removing the housing 12 from the encasement 50, and is preferably aligned with the aperture 30.

In use, the housing 12 functions as a prosthetic breast generally for a person who has had a mastectomy. A fluid, preferably water, may be selectively added into or removed from the housing 12 until the housing 12 has a desired size. The desired size is typically that such the housing 12 has the same shape as a remaining breast. Because of variations in breast size, it is preferred that the housing 12 is offered in a plurality of shapes and sizes though the measurements delineated above are considered optimal. The opening 22 may be used for both the quick filling and emptying of the housing 12. Because the opening 22 is closed with a simple plug 24, it is positioned in the back wall 14 so that the wearer's chest will ensure that the plug 24 remains in the opening 22 to ensure that no leaks occur. However, once the wearer has the device 10 in its proper position, adjustments to size may yet be required. This is simply handled with the injector 34 which is used for adding additional fluid, though the injector 34 may also be used for removing fluid as the valve would be opened when the nozzle 36 is inserted into the aperture 30. The covering 44 is an additional insurance measure to prevent leakage of fluid through the aperture 30 while adding to the device 10 the look of an areola and nipple combination of a breast.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A prosthetic breast kit comprising:

a housing having a back wall having a peripheral edge, a front wall being attached to and extending along a length of said peripheral edge such that an inner space is defined between said front and back walls, said front wall having a convex shape such that said front wall extends outwardly away from said back wall, said housing having an opening therein, said back wall and said front wall comprising a latex material having a thickness generally between 0.08 mm and 2.0 mm, wherein said front wall has an aperture extending therein, said aperture being generally centrally located in said front wall;

a plug being removably extendable into opening;

an injector for selectively injecting fluid into said housing including a nozzle fluidly coupled to a container, said nozzle being removably extendable into said aperture for delivering fluid from said container into said housing, a one way valve being fluidly coupled to said aperture and being positioned within said inner space for preventing fluid within said housing from extending said housing through said aperture;

a covering for selective positioning over and closing said aperture, a nub being attached to said covering and generally being centered thereon such that said nub extends away from said housing when said covering is positioned over said aperture; and wherein a fluid may be selectively added into or removed from said housing until said housing has a desired size.

2. The kit according to claim 1, wherein said opening is positioned in said back wall.

3. The kit according to claim 1, wherein said latex has an ultimate elongation capability greater than 400% and a tensile strength greater than 12 MPa.

4. The kit according to claim 3, wherein said latex comprising a nitrile polymer.

5. The kit according to claim 1, wherein said back wall has perimeter length generally between 25 cm and 50 cm and a maximum distance between inner surfaces of said front and back walls is generally between 6 cm and 12 cm when said front and back walls are in a relaxed state.

6. The kit according to claim 1, wherein said aperture is positioned within a generally circular depression in an outer surface of said front wall, said covering includes a disc member having a shape adapted for positioning within said depression, said disc member having a greater thickness than a depth of said depression such that said disc extends above said outer surface of said front wall when said disc is positioned within said depression, wherein said nub is attached to said disc and is generally centered thereon.

7. The kit according to claim 1 further including an encasement being positioned over said housing, said encasement comprising an elastic cloth material, said encasement having at least one opening therein.

8. A prosthetic breast kit comprising:

a housing having a back wall having a peripheral edge, a front wall being attached to and extending along a length of said peripheral edge such that an inner space is defined between said front and back walls, said front wall having a convex shape such that said front wall extends outwardly away from said back wall, said housing having an opening therein, said opening being positioned in said back wall, said back wall and said front wall comprising a latex material having a thickness generally between 0.08 mm and 2.0 mm, said latex having an ultimate elongation capability greater than 400%, said latex having a tensile strength greater than 12 MPa, said latex comprising a nitrile polymer, said back wall having perimeter length generally between 25 cm and 50 cm, a maximum distance between inner surfaces of said front and back walls being generally between 6 cm and 12 cm when said front and back walls are in a relaxed state, said front wall having an aperture extending therein, said aperture being generally centrally located in said front wall, said aperture being positioned within a generally circular depression in an outer surface of said front wall;

a plug being removably extendable into opening;

an injector for selectively injecting fluid into said housing including a nozzle fluidly coupled to a container, said nozzle being removably extendable into said aperture for delivering fluid from said container into said housing;

a covering for selective positioning over and closing said aperture, said covering including a disc member having a shape adapted for positioning within said depression, said disc member having a greater thickness than a depth of said depression such that said disc extends above said outer surface of said front wall when said disc is positioned within said depression, a nub being attached to said disc and generally centered thereon such that said nub extends away from said housing when said disc is positioned within said depression;

a one way valve being fluidly coupled to said aperture and being positioned within said inner space for preventing fluid within said housing from exiting said housing through said aperture; and wherein a fluid may be selectively added into or removed from said housing until said housing has a desired size.

9. A prosthetic breast device comprising:

a housing having a back wall having a peripheral edge, a front wall being attached to and extending along a length of said peripheral edge such that an inner space is defined between said front and back walls, said front wall having a convex shape such that said front wall extends outwardly away from said back wall, said housing having an opening therein, said opening being positioned in said back wall, said back wall and said front wall comprising a latex material having a thickness generally between 0.08 mm and 2.0 mm, said front wall having an aperture extending therein, said aperture being generally centrally located in said front wall, said aperture being positioned within a generally circular depression in an outer surface of said front wall;

a plug being removably extendable into opening;

a covering for selective positioning over and closing said aperture, said covering including a disc member having a shape adapted for positioning within said depression, said disc member having a greater thickness than a depth of said depression such that said disc extends above said outer surface of said front wall when said disc is positioned within said depression, a nub being attached to said disc and generally centered thereon such that said nub extends away from said housing when said disc is positioned within said depression;

a one way valve being fluidly coupled to said aperture and being positioned within said inner space for preventing fluid within said housing from exiting said housing through said aperture; and wherein a fluid may be selectively added into or removed from said housing until said housing has a desired size.

10. The device according to claim 9, further including an encasement being positioned over said housing, said encasement comprising an elastic cloth material, said encasement having at least one opening therein.

\* \* \* \* \*